United States Patent [19]

Place et al.

[11] Patent Number: 5,147,654

[45] Date of Patent: Sep. 15, 1992

[54] ORAL OSMOTIC DEVICE FOR DELIVERING NICOTINE

[75] Inventors: Virgil A. Place, Kawaihe, Hi.; Patrick S. L. Wong, Palo Alto, Calif.; Brian L. Barclay; Jerry D. Childers, both of Sunnyvale, Calif.

[73] Assignee: ALZA Corporation, Palo Alto, Calif.

[21] Appl. No.: 793,058

[22] Filed: Nov. 15, 1991

Related U.S. Application Data

[63] Continuation-in-part of Ser. No. 557,434, Jul. 23, 1990, abandoned.

[51] Int. Cl.$^5$ ............................................. A61K 9/24
[52] U.S. Cl. .................................... 424/473; 424/435; 424/478
[58] Field of Search ...................... 424/473, 435, 478

[56] References Cited

U.S. PATENT DOCUMENTS

| | | | |
|---|---|---|---|
| 3,732,865 | 5/1973 | Higuchi et al. | 128/260 |
| 3,845,217 | 10/1974 | Ove Birger Ferno et al. | 426/3 |
| 3,845,770 | 11/1974 | Theeuwees et al. | 128/260 |
| 3,901,248 | 8/1975 | Lichtneckert et al. | 131/2 |
| 3,916,899 | 11/1975 | Theeuwes et al. | 128/260 |
| 4,111,202 | 9/1978 | Theeuwes | 128/260 |
| 4,238,475 | 12/1980 | Witzel et al. | 424/48 |
| 4,327,725 | 5/1982 | Cortese et al. | 128/260 |
| 4,572,832 | 2/1986 | Kigasawa et al. | 424/19 |
| 4,597,961 | 7/1986 | Etscorn | 424/28 |
| 4,612,008 | 9/1986 | Wong et al. | 604/892 |
| 4,639,368 | 1/1987 | Niazi et al. | 424/48 |
| 4,666,705 | 5/1987 | DeCrosta et al. | 424/482 |
| 4,713,243 | 12/1987 | Schiraldi et al. | 424/151 |
| 4,725,440 | 2/1988 | Ridgway et al. | 424/465 |
| 4,758,434 | 7/1988 | Kydonieus et al. | 424/449 |
| 4,764,378 | 8/1988 | Keith et al. | 424/435 |
| 4,781,924 | 11/1988 | Lee et al. | 424/449 |
| 4,783,337 | 11/1988 | Wong et al. | 424/468 |
| 4,806,356 | 2/1989 | Shaw | 424/440 |
| 4,837,027 | 6/1989 | Lee et al. | 424/449 |
| 4,940,587 | 7/1990 | Jenkins et al. | 424/480 |
| 5,021,053 | 6/1991 | Barclay et al. | 604/892.1 |

OTHER PUBLICATIONS

"Treatment of denture stomatitis by a sustained drug-delivery device: a preliminary study", J. Dent. (1988) vol. 16, pp. 219-221, D. J. Lamb & C. W. I. Douglas.

"Candidosis of the Oral Cavity", Drugs, vol. 36, pp. 633-642 (1988) K. D. Hay.

"Combination of Behavioral Smoking Cessation Therapy with Transdermal Nicotine Substitution: Long-Term Effects," Smoking & Health 1987; Proceedings of the 6th World Conference on Smoking & Health, Tokyo, 9-12 Nov. 1987, pp. 857-860, Buchkremer G., Bents H., Minneker E., Optiz K.

"Nicotine Replacement: The Role of Blood Nixcotine Levels, Their Rate of Change, and Nicotine Tolerance Progress In Clinical and Biological Research; Nicotine Replacement: A Critical Evaluation", pp. 63-94 (1988) Michael A. H. Russell.

Primary Examiner—Thurman K. Page
Assistant Examiner—D. Gabrielle Phelan
Attorney, Agent, or Firm—D. Byron Miller; Edward L. Mandell; Steven F. Stone

[57] ABSTRACT

An osmotic device (10) for the controlled systemic delivery of nicotine through an oral mucosal membrane of a human patient is disclosed. The device (10) has a size and shape adapting it to be comfortably retained in the mouth for extended periods of time. The device (10) comprises a semipermeable wall (12) surrounding a compartment (13) containing a nicotine salt (14) and optionally an alkaline salt which is capable of reacting with the nicotine salt in the presence of water to form nicotine base. The conversion of nicotine salt to nicotine base may take place within the device (10) and/or outside the device and in the patient's mouth. Nicotine base and/or salt is delivered from the compartment (13) through a passageway (17) in the wall (12). The nicotine salt exhibits good stability and shelf life while the nicotine base exhibits excellent absorption through oral mucosal membranes.

74 Claims, 1 Drawing Sheet

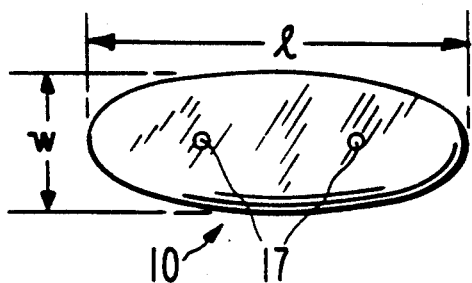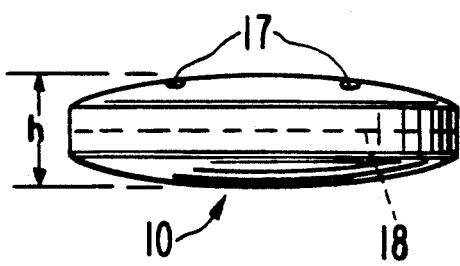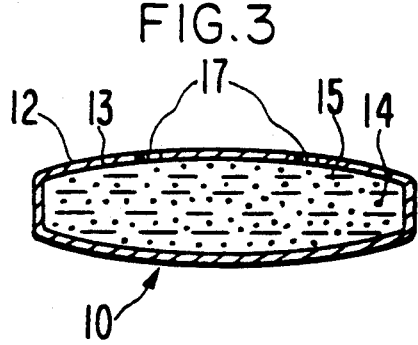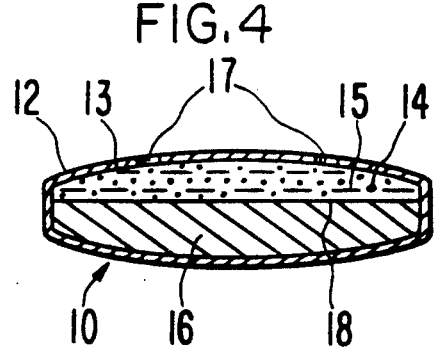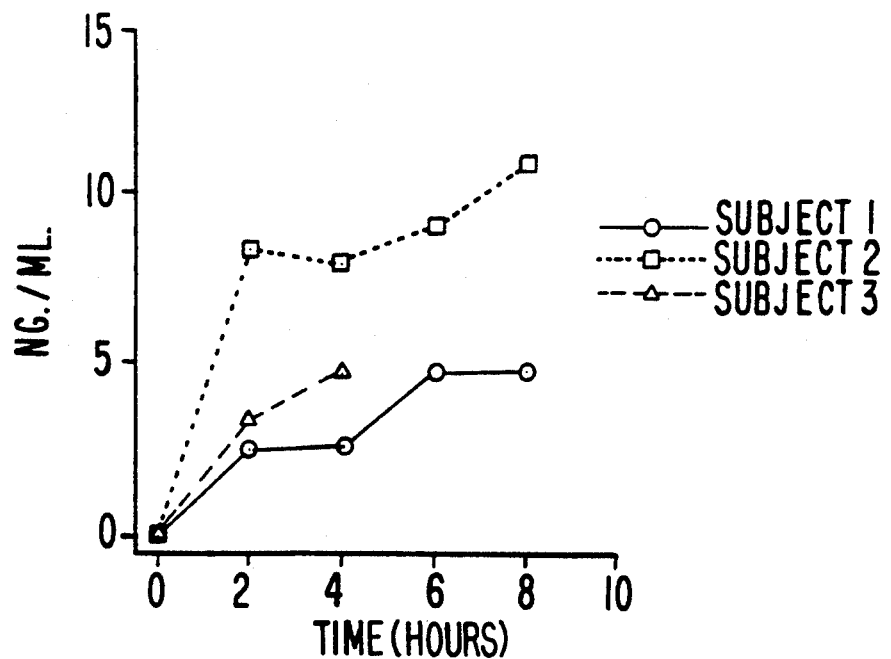

ORAL OSMOTIC DEVICE FOR DELIVERING NICOTINE

CROSS-REFERENCE TO RELATED APPLICATIONS

This application is a continuation-in-part of U.S. application Ser. No. 07/557,434 filed Jul. 23, 1990 and now abandoned and benefit of the filing date of said earlier filed application is claimed under 35 USC § 120. This application is related to U.S. Pat. No. 5,021,053 issued Jun. 4, 1991, and U.S. Pat. No. 5,053,032 issued Oct. 1, 1991. These patents are assigned of record to ALZA Corporation.

1. Technical Field

This invention pertains to an osmotic device for systemically delivering nicotine to a patient. More particularly, the invention relates to an osmotic device for systemically delivering nicotine base through the oral mucosal membranes of a patient.

2. Background Art

Systemic delivery of nicotine has been suggested as a treatment for smoking cessation. See "Longterm Effects of Transdermal Nicotine Substitution in Behavioral Smoking Cessation, " G. Buchkremer et al, Abstracts 6th World Conference on Smoking and Health, Nov. 9-12, 1987, Tokyo, Japan and "Nicotine Replacement: The Role of Blood Nicotine Levels, Their Rate of Change, and Nicotine Tolerance," M. Russell, Nicotine Replacement: A Critical Evaluation, pp 79-83 (1988). To date, nicotine replacement for smoking cessation has taken two forms: nicotine-containing chewing gum and transdermal nicotine delivery systems. See for example U.S. Pat. Nos. 3,845,217; 3,901,248; 4,597,961 and 4,758,434. In summary, the prior art has taught both the transdermal delivery of nicotine and the trans-oral-mucosal membrane delivery of nicotine from chewing gum as an aid to smoking cessation.

When administering nicotine buccally from a chewing gum (i.e., by absorption of the drug through the highly vascularized buccal tissues of the mouth), a number of conditions are present which make it difficult to effectively deliver the nicotine in a controlled and therapeutically effective amount for a prolonged period of time (e.g., for periods greater than several minutes). The rate and vigor of chewing can vary greatly from patient to patient, thereby making controlled delivery of the nicotine nearly impossible. A further problem with chewing gums is that the patient's jaws become tired after extended chewing. This severely limit the time period for nicotine delivery.

The prior art has also suggested oral delivery of drugs using lozenges and pastilles. For example, when a patient is given a drug-containing lozenge, there is a natural tendency to suck and chew on the lozenge. Chewing can greatly reduce the time that the lozenge remains in the patient's mouth and thereby effectively reduces the time period during which the drug can be buccally administered by the lozenge. In addition, the action of saliva and swallowing by the patient effectively reduces the concentration of drug along the buccal membranes of the oral cavity and further causes much of the drug to be swallowed. Many drugs, once swallowed, are rendered inactive upon encountering the low Ph environment of the stomach. While a certain percentage of the swallowed drug is absorbed from the gastrointestinal tract into the bloodstream, in the case of nicotine, most of the absorbed drug is rendered inactive by the hepatic first-pass metabolism in the liver.

In response to the problem of short duration of drug delivery from lozenges, pastilles and chewing gums, the use of an osmotic pump to deliver medication to the buccal tissues has been suggested. The most elementary osmotic pumps can be formed by compressing a tablet of an osmotically active drug (or an osmotically in active drug in combination with an osmotically active agent or osmagent) and then coating the tablet with a semipermeable membrane which is permeable to aqueous-based saliva but impermeable to the passage of drug and/or osmagent. One or more delivery orifices are formed through the semipermeable membrane wall. In operation, fluid is imbibed through the semipermeable membrane wall and contacts the drug and/or salt to form a solution or suspension of the drug. The drug solution or suspension is then pumped out through the orifice as fresh fluid is imbibed through the semipermeable membrane. While the use of osmotic pumps has proven to be very successful in delivering drugs through the gastrointestinal (GI) tract (i.e., by swallowing the device), there are several problems with buccal administration. As with drug-containing lozenges, there is a natural tendency for the patient to suck and chew on the drug-containing osmotic pump. Chewing in particular tends to compress the deformable membrane wall, thereby squeezing the drug solution or suspension out of the device at an accelerated rate. In some cases, chewing can crack the membrane wall causing the drug to be released into the mouth at higher than the desired rate. The duration of drug delivery is thereby severely curtailed. For example, when an osmotic pump, designed to deliver drug at a relatively constant rate over a period of 12 to 24 hours within the GI tract, is placed in the oral cavity and subjected to patient sucking and chewing, the device delivers the entire drug dose relatively quickly, sometimes in less than an hour.

Thus, there has been a need for àn oral nicotine dosage form which is osmotically driven but which is able to continuously deliver nicotine within the mouth to the buccal membranes and which is relatively unaffected by the patient sucking and chewing on the device.

The osmotic device disclosed in U.S. Pat. No. 5,021,053 is designed specifically to deliver drug at a controlled rate into the mouth of a patient, either for local or systemic delivery through the buccal tissues. This device includes a drug layer containing e.g., nicotine base, and a layer of an expandable hydrogel. In operation, the hydrogel expands in the presence of external fluid that is imbibed into the device. Likewise, the imbibed fluid forms a solution or suspension of the drug that is dispensed from the device through the passageway as the hydrogel expands. This device operates successfully for its intended use, and it delivers many difficult to deliver beneficial agents for their intended purpose.

Another proposed solution to the problem of short duration of drug delivery from lozenges, pastilles, and chewing gums, has been a delivery device comprised of a hydrophilic polymer matrix containing drug dispersed in the matrix. When the matrix is placed between the cheek and gum of a patient, the hydrophilic polymer absorbs moisture from saliva and from the buccal membrane, eventually adhering itself to the membrane surface. While it is desirable from the standpoint of patient comfort and convenience to adhere the delivery platform directly to the buccal membrane, this can create a problem when delivering a drug such as nicotine. Because the hydrophilic matrix adheres to the membrane surface, the membranes adjacent the matrix are continuously exposed to high concentrations of drug. In the case of nicotine, these high concentrations can cause irritation.

Thus, there has been a need for an oral nicotine dosage form which is able to continuously deliver nicotine transmucosally for extended periods of time without causing irritation.

Nicotine is generally in either free base or in salt form. Nicotine base is readily absorbed through skin and mucosal membranes. Unfortunately, nicotine base is highly unstable and is difficult to contain using conventional barrier packaging materials. For example, transdermal delivery systems containing nicotine base cannot be packaged in conventional water-impermeable plastic wrapping materials since the nicotine base easily permeates through conventional barrier packaging materials. Nicotine salts, on the other hand, are extremely stable. Pharmaceutically acceptable nicotine salts include nicotine hydrochloride, nicotine dihydrochloride, nicotine, sulfate, nicotine bitartrate, nicotine zinc chloride monohydrate and nicotine salicylate. Nicotine salts, however, are not readily absorbed through skin or mucosal membranes. Accordingly, transdermal nicotine delivery devices which stored nicotine in a form suitable for absorption through the skin (i.e., in free base form) had an undesirably short shelf life and presented difficult packaging problems. While the shelf life and packaging problems could be overcome by incorporating a nicotine salt into the transdermal delivery devices, such a device would have had an undesirably low nicotine delivery rate through the skin. This dilemma has been overcome in the transdermal nicotine delivery field by incorporating an activating compound which converts the nicotine salt into nicotine base in situ. See U.S. Pat. Nos. 4,781,924 and 4,837,027.

3. Disclosure of the Invention

Accordingly, it is an object of this invention to provide an osmotic device for the controlled systemic delivery of nicotine to a human, for an extended period of time.

It is another object of the invention to provide a delivery device capable of delivering nicotine to the systemic circulation at levels sufficient to reduce the urge to smoke.

It is another object of the invention to provide an oral osmotic device useful for systemically delivering nicotine through the oral mucosal (i.e., buccal) membranes of a patient.

It is another object of the invention to provide an oral osmotic therapeutic device that can administer nicotine into the oral cavity for an extended period of time without causing irritation to the oral mucosal membranes.

It is a further object of the invention to provide an oral osmotic device useful for systemically delivering nicotine in a form which is readily absorbable through the oral mucosal membranes but which as good stability, long shelf life and presents no serious packaging problems prior to actual use.

Other objects, features and advantages of the invention will be more apparent to those versed in the art from the following detailed specification taken in conjunction with the figures and the accompanying claims.

This invention concerns an osmotic device for controlled systemic delivery of nicotine through the oral mucosal membranes in the oral cavity of a human. The device comprises a shaped wall which surrounds and forms a compartment containing a nicotine salt which is capable of reacting in the presence of an aqueous fluid to form nicotine base. The wall is formed of a material which is permeable to the passage of an aqueous fluid present in the oral cavity (e.g., saliva). The wall material is substantially impermeable to the passage of nicotine salt. One or more passageways through the wall are provided for delivering the nicotine salt and/or the nicotine base formed in the compartment to the oral cavity.

Preferred nicotine salts include nicotine hydrochloride, nicotine dihydrochloride, nicotine sulfate, nicotine monotartrate, nicotine bitartrate, nicotine zinc chloride monohydrate and nicotine salicylate. Nicotine monotartrate and nicotine bitartrate are most preferred.

Preferably, the compartment also contains an alkaline salt, whereby the nicotine salt and the alkaline salt are capable of reacting in the presence of the aqueous fluid to form nicotine base. Preferred alkaline salts include sodium carbonate, sodium bicarbonate, potassium carbonate, potassium bicarbonate, trisodium phosphate, disodium hydrogen phosphate, sodium oxylate, sodium succinate, sodium citrate, and sodium salicylate. Sodium bicarbonate is most preferred.

In operation, the aqueous fluid present in the oral cavity (e.g., saliva) permeates through the wall into the compartment, initiating a chemical reaction with the nicotine salt resulting in the formation of nicotine base. As fresh fluid permeates through the wall, the nicotine base is "pumped" through the passageway in the wall and into the oral cavity where it is quickly absorbed through the oral mucosal membranes. In those embodiments wherein the compartment contains no alkaline salt, the conversion of the nicotine salt to nicotine base may take place predominantly within the oral cavity outside the osmotic device. Thus, in these embodiments, a solution or suspension of the nicotine salt, optionally with some nicotine base which is converted within the compartment, is "pumped" through the passageway in the wall and into the oral cavity. Once in the oral cavity, the nicotine base is absorbed through the mucosal membranes.

The compartment preferably further contains a layer of an expandable driving member formed of a water-swellable hydrophilic polymer. The wall material is substantially impermeable to the hydrophilic polymer. The hydrophilic polymer absorbs fluid imbibed into the compartment, and can expand from a rested to an expanded state. The hydrophilic polymer is in contact with the nicotine/alkaline salt formulation and positioned distant from the passageway. Nicotine base is released from the device by the combined actions of fluid being imbibed through the wall into the compartment, and by fluid being imbibed by the hydrophilic polymer causing it to expand and increase in volume, thereby exerting a force against the reacting salts/nicotine base reaction product that decreases their respective volume, whereby the nicotine base and/or nicotine salt in solution or suspension is released through the passageway at a rate controlled by the permeability of the wall, the osmotic pressure gradient across the wall, and the rate of expansion of the driving hydrophilic polymer over a prolonged delivery period. The device has a size and shape allowing it to be comfortably retained in the oral cavity for an extended period of time.

4. Brief Description of the Drawings

FIG. 1 is a top view of an osmotic device for systemically administering nicotine base through the oral mucosal membranes of the oral cavity;

FIG. 2 is a side view of the oral osmotic device shown in FIG. 1;

FIG. 3 is a side sectional view of one embodiment of the osmotic device of the present invention illustrating the internal structure of the device;

FIG. 4 is a side sectional view of another embodiment of the osmotic device of the present invention illustrating a preferred alternative internal structure;

FIG. 5 is a graph depicting the blood plasma concentration of nicotine in human subjects treated with a device according to the present invention.

In drawings (which are not drawn to scale) and the specification, like parts in related figures are identified by like numerals.

5. Modes for Carrying Out the Invention

Turning now to the drawings, an osmotic device suitable for the controlled transmucosal systemic delivery of nicotine base through an oral mucosal membrane is shown in FIGS. 1 and 2, and is indicated by the numeral 10. Device 10 has a wall 12 that surrounds and forms a compartment 13, as seen in the sectional views of FIGS. 3 and 4. Wall 12 is formed of a polymeric material that is substantially permeable to the passage of saliva and substantially impermeable to the passage of nicotine salt. The polymer forming wall 12 is non-toxic and it maintains its physical and chemical integrity during the life of device 10. Device 10 delivers nicotine base through one or more passageways 17 through wall 12.

In the embodiment shown in FIG. 3, compartment 13 contains a nicotine salt 14. Preferably, compartment 13 contains both a nicotine salt and an alkaline salt, both of which are identified by dots 14, that can be from insoluble to very soluble in an exterior aqueous fluid (saliva), indicated by dashes 15. When either the nicotine salt or the alkaline salt is soluble in fluid 15, an osmotic pressure gradient is formed across wall 12 and the aqueous based saliva 15 will be imbibed into compartment 13. Alternatively, if both th nicotine salt and the alkaline salt have only limited solubility or are substantially insoluble in fluid 15, they can be mixed with an osmagent that is soluble in fluid and exhibits an osmotic pressure gradient across wall 12 against the fluid.

According to the present invention a therapeutic nicotine delivery device is provided in which the device initially contains a storage stable nicotine salt which is converted to nicotine base is after the device is placed in the oral cavity. The nicotine base is the preferred form of nicotine for systemic transmucosal delivery since it is quickly absorbed through the oral mucosal membranes. The conversion of the nicotine salt to nicotine base is accomplished by reacting the nicotine salt with water at an alkaline pH, i.e., at a pH above about 7. Under normal conditions, the pH of saliva ranges from about 5.6 to 7.6. In those individuals having a saliva pH above about 7, it may not necessary to add an alkaline salt to the nicotine formulation 14. However, in order to insure good conversion of the nicotine salt to nicotine base, it is greatly preferred to add an alkaline salt within compartment 13. Suitable alkaline salts include pharmaceutically acceptable salts having a pH of greater than about 7.0 in a 0.5M aqueous solution. Most preferably, the alkaline salt is soluble in the aqueous based fluid. Specific examples of preferred alkaline salts include sodium carbonate, sodium bicarbonate, potassium carbonate, potassium bicarbonate, trisodium phosphate, disodium hydrogen phosphate, sodium oxylate, sodium succinate, sodium citrate and sodium salicylate. Of these, sodium bicarbonate is most preferred.

Suitable nicotine salts include pharmaceutically acceptable nicotine salts, such as nicotine hydrochloride, nicotine dihydrochloride, nicotine sulfate, nicotine monotartrate, nicotine bitartrate, nicotine zinc chloride monohydrate and nicotine salicylate. Most preferred are nicotine monotartrate and nicotine bitartrate.

In operation, device 10 is placed in the oral cavity of a patient where it is exposed to aqueous biological fluids (e.g., saliva). The saliva permeates through wall 12 towards osmotic equilibrium. As the aqueous fluid enters compartment 13, a chemical reaction is initiated with the aqueous fluid, and preferably between the nicotine salt, the alkaline salt and the aqueous fluid. Two examples of such a chemical reaction, the first involving no alkaline salt and the second involving the alkaline salt sodium bicarbonate, are shown below:

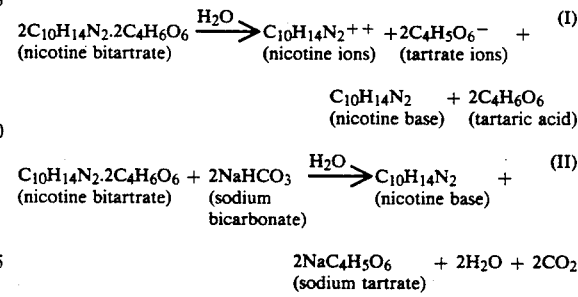

As can be seen from the above, device 10 initially contains a nicotine salt (e.g., nicotine bitartrate). The nicotine salt has excellent stability. Accordingly, device 10 is storage stable and easily packaged. Once placed in use in an aqueous environment (e.g., in the oral cavity) the nicotine salt is converted to nicotine base. The nicotine salt may be converted to nicotine base either within device 10, outside of device 10 and within the oral cavity, or a combination of the two. Thus, nicotine, either in the form of a salt solution/suspension which is later converted to nicotine base in the oral cavity and/or nicotine in the form of nicotine base which is converted from the nicotine salt within the device 10, is delivered from the device 10 through passageways 17. The nicotine base which forms and is delivered into the oral cavity is readily absorbable by the oral mucosal membranes.

In a preferred embodiment shown in FIG. 4, compartment 13 also contains a layer of an expandable driving member 16 composed of a hydrophilic polymer, optionally cross-linked, which possesses osmotic properties such as the ability to imbibe aqueous fluid and exhibit an osmotic pressure gradient across the wall 12 against the fluid. Wall 12 is substantially impermeable to the passage of the hydrophilic polymer in driving layer 16. Layer 16 absorbs fluid imbibed into the compartment and swells. The osmotic pressure of the hydrophilic polymer network is the driving force of the swelling, expanding layer 16. As shown in FIG. 4, layer 16 is in contact with the layer containing the nicotine/alkaline salt formulation and at the interface 18, a thin precipitate preferably forms. The precipitate is especially preferred when the nicotine salt is soluble in the imbibed fluid. The precipitate forms in the presence of a solution containing he nicotine salt and the alkaline salt, and it is substantially impervious and restricts the passage of nicotine salt, alkaline salt and nicotine base into layer 16. The precipitate further serves as an in situ formed membrane integral with the hydrophilic polymer for applying pressure against the reacting nicotine-/alkaline salts during operation of device 10. When the nicotine and alkaline salts are substantially insoluble, interface 18 can be achieved simply by maintaining a difference in the viscosity values of layers 14 and 16. For example, layer 16 can be formulated with a hydrophilic polymer having a high molecular weight and a high degree of cross-linking. In such a case, there is negligible penetration of the insoluble suspension into layer 16.

Device 10 releases nicotine base and/or salt by aqueous fluid (e.g., saliva) being imbibed into compartment 13 in a tendency towards osmotic equilibrium at a rate determined by the permeability of wall 12 and the osmotic pressure gradient across wall 12. These operations include the nicotine base and/or salt being pumped out of device 10 through passageways 17 due to the continuous permeation of fresh aqueous fluid into compartment 13. In those embodiments which utilize a hydrophilic polymer layer 16, device 10 releases nicotine base and/or salt by a combination of the above-described pumping phenomenon and by the hydrophilic polymer layer 16 swelling and applying pressure against the reacting salts/nicotine base reaction product thereby delivering the nicotine base and/or salt out of device 10 through passageways 17.

Device 10 is designed for delivering nicotine base through the oral mucosal membranes over an extended period of time. Because the device is designed to be retained in the mouth for periods on the order of about 0.5 to 12 hours, the device must have an exterior shape which is comfortably retained in the mouth. It has been found that an oblong or elliptically shaped device 10 is preferred from a comfort standpoint. As shown in FIGS. 1 and 2, device 10 has a length l, a width w, and a height h. It has been found that devices 10 having an aspect ratio, which ratio is the ratio of l:w, of about 1.2:1 to about 3:1 are most comfortably retained in the human mouth. Preferably, the device 10 has an aspect ratio of about 1.3:1 to about 2:1, and most preferably about 1.5:1 to about 1.7:1. In addition, in order to fit comfortably between the cheek and gum of a patient, the device has a height of about 0.5 to about 10 mm, preferably about 2 to about 8 mm, and most preferably about 3 to about 5 mm. The device also has a volume of less than about 2 cm$^3$, preferably about 0.1 to about 0.5 cm$^3$, and most preferably about 0.25 cm$^3$.

Osmotic delivery device 10 optionally has a mechanism for displaying the amount of nicotine/alkaline salt formulation 14 remaining in the device for delivery into the patient. In one preferred embodiment shown in FIG. 2, the display means comprises a color contrast between the nicotine/alkaline salt formulation 14 and the driving layer 16, in combination with a translucent wall 12. In this embodiment, the color of the nicotine-/alkaline salt formulation 14 is chosen to provide good visual contrast with the color of the driving layer 16. The color of the salt formulation 14 can be achieved using any number of coloring techniques known in the art. A number of pharmaceutically acceptable dyes or coloring agents may be mixed with either the salt formulation 14 and/or the driving layer 16 in order to provide the appropriate color contrast. Suitable pharmaceutically acceptable coloring agents, both natural and synthetic, are known in the art. See *Remington's Pharmaceutical Sciences*, 14th Ed., pp 1319-21.

In accordance with this embodiment of the invention, the patient can easily determine the amount of nicotine-/alkaline salt formulation 14 remaining in compartment 13 simply by visually inspecting device 10. For example, the salt formulation 14 may have a white color and the layer 16 may be dyed to achieve a red color. When the device is first placed in the mouth of the patient, the white and red layers are clearly visible through the translucent semipermeable wall 12. After a period of time in the patient's mouth, the device 10 will imbibe aqueous fluid (e.g., saliva) thereby causing a reaction between the nicotine and alkaline salts and water, causing nicotine base to be formed and also causing the hydrogel 16 layer to expand. Because the salt formulation layer and the hydrophilic polymer layer have contrasting colors, the patient can easily determine the relative amount of nicotine/alkaline salt formulation remaining in the device for delivery. When only the red hydrophilic polymer layer remains, the patient it alerted that the device 10 has delivered all of the nicotine. This can be checked simply by visually inspecting the device.

In another preferred embodiment of the present invention, the mechanism for signaling the patient comprises a contrast in taste between the nicotine/alkaline salt formulation 14 and the hydrophilic polymer driving layer 16. In this embodiment, the flavor of the salt formulation 14 is chosen to provide a sharp contrast with the flavor of the hydrophilic polymer driving layer 16. Preferably, the salt formulation contains a flavoring agent which is enjoyed by the patient, while the hydrophilic polymer layer contains a flavoring agent having an unpleasant taste. For example, the nicotine/alkaline salts can be flavored with peppermint oil while the hydrophilic polymer layer is flavored with an edible salt (e.g., NaCl). The flavoring of the salt formulation 14 can be achieved by any number of flavoring techniques known in the art. Any number of pharmaceutically acceptable flavoring agents may be mixed with either the salt formulation 14 and/or the hydrophilic polymer in layer 16 in order to provide the appropriate taste contrast. Suitable pharmaceutically acceptable flavoring agents, both natural and synthetic, are known in the art. See Remington's Pharmaceutical Sciences, 14the Ed., pp 1321-1338.

Osmotic delivery device 10 can be manufactured with a wall 12 formed of a material that does not adversely affect the salts 14, the osmagent, if any is present, and the hydrophilic polymer in layer 16 if layer 16 is present. The material forming wall 12 should also not adversely affect the buccal tissues of the patient. In addition, the material forming wall 12 is permeable to the passage of aqueous biological fluids naturally present in the oral cavity (e.g., saliva), while remaining essentially impermeable to the passage of the nicotine salt, the alkaline salt, and the hydrophilic polymer. The selectively permeable materials forming wall 12 are insoluble in fluids naturally present in the oral cavity. Typical materials for forming wall 12 include semipermeable polymers known to the art as osmosis and reverse osmosis membranes, such as cellulose acylate, cellulose diacylate, cellulose triacylate, cellulose acetate, cellulose diacetate, cellulose triacetate, agar acetate, amylose triacetate, beta glucan acetate, acetaldehyde dimethyl acetate, cellulose acetate ethyl carbamate, polyamides, polyurethanes, sulfonated polystyrenes, cellulose acetate phthalate, cellulose acetate methyl carbamate, cellulose acetate succinate, cellulose acetate dimethylaminacetate, cellulose acetate ethyl carbamate, cellulose acetate chloracetate, cellulose dipalmatate, cellulose dioctanoate, cellulose dicaprylate, cellulose dipentanlate, cellulose acetate valerate, cellulose acetate succinate, cellulose propionate succinate, methylcellulose, cellulose acetate p-toluene sulfonate, cellulose acetate butyrate, cross-linked selectively semipermeable polymers formed by the coprecipitation of a polyanion and a polycation as disclosed in U.S. Pat. Nos. 3,173,876; 3,276,586; 3,541,005; 3,541,006; and 3,546,142, semipermeable polymers as disclosed by Loeb and Sourirajan in U.S. Pat. No. 3,133,132, lightly cross-linked polystyrene derivatives, cross-linked poly(sodium styrene sulfonate), poly(vinylbenzyltrimethyl ammonium chloride), cellulose acetate having a degree of substitution up to 1 and an acetyl content up to 21%, cellulose diacetate having a degree of substitution of 1 to 2 and an acetyl content of 21 to 35%, cellulose triacetate having a degree of substitution of 2 to 3 and an acetyl content of 35 to 44.8%, as disclosed in U.S. Pat. No. 4,160,020. Generally, semipermeable materials useful for forming wall 12 will have a fluid permeability of $10^{-5}$ to $10^{-1}$ (cc·mil/cm$^2$·hr·atm) expressed per atmosphere of hydrostatic or osmotic pressure difference across semipermeable wall 12.

In accordance with one preferred embodiment of the present invention, the material forming wall 12 is sufficiently translucent to allow a patient to see the relative amounts of hydrophilic polymer 16 and salts 14 remaining in compartment 13. Examples of suitable translucent materials include the cellulosic polymers mentioned above. Generally, the wall 12 will contain a sufficient amount of translucent material to enable the patient to see the salt layer 14 and the hydrophilic polymer layer 16 within compartment 13. Suitable amounts of translucent materials will depend upon the translucency of the wall material, the methods and conditions under which the wall materials are formed, as well as the amount of contrast in the colors of the drug and hydrogel layers. Suitable amounts of translucent materials can be easily determined through routine experimentation using the example herein.

In order to withstand the conditions of use of within the oral cavity (i.e., patient sucking and chewing of the delivery device), the salt layer 14 preferably contains a gelling or suspending agent which prevents the exterior wall 12 from collapsing during use. Representative gelling or suspending agents include acacia, agar-agar, calcium carrageenan, alginic acid, algin, alginates, agarose powder, collagen, colloidal magnesium silicate, colloidal silicon dioxide, sodium carboxymethylcellulose, partially cross-linked polyacrylic acid, polyvinyl pyrrolidone, hydroxyethylcellulose, hydroxypropylcellulose, hydroxypropylmethylcellulose, polyethylene oxide, pectin, gelatin, calcium silicate and mixtures thereof.

Generally, the salt layer 14 may contain from about 5 to about 90 wt % of a gelling or suspending agent, depending on the loading of salts in layers 14 and their solubility in the fluid entering the device. Most preferably, the gelling or suspending agent is polyethylene oxide hydroxypropylmethylcellulose or mixtures thereof.

Other agents which can optionally be mixed with salts 14 include binder, dispersants, wetting agents and lubricants. Representative of these include binders like polyvinyl pyrrolidone, and hydroxypropylmethylcellulose, wetting agents such as fatty amines and fatty quaternary ammonium salts, and lubricants such as magnesium stearate and stearic acid. The phrase salt formulation indicates that the nicotine and alkaline salts can be present in the compartment either alone, or in admixture with a gelling or suspending agent, an osmagent, a binder, a dye or the like.

Device 10 should deliver nicotine to the oral mucosal membranes at levels sufficient to reduce the urge to smoke. In general, the nicotine delivery rate should be high enough to saturate the nicotine binding sites in the oral mucosal membranes, yet not so high as to cause mucosal tissue irritation or undesirable sensations. A number of studies have been conducted in order to determine the optimal nicotine delivery rate for achieving the desired result of reduction of the urge to smoke and also to minimize irritation. Optimally, nicotine delivery should be within the range of about 250 to 4000 μg/hr, preferably about 500 to 2000 μg/hr and most preferably about 1000 μg/hr. In this manner, the target blood level to reduce the urge to smoke, which for most smokers is about 3 to 20 ng/ml, can be attained.

The optional osmagent, present when both the nicotine salt and the alkaline salt are not themselves osmotically active, is an osmotically effective compound soluble in the fluid that enters the device, and which exhibits an osmotic pressure gradient across the semipermeable wall against the aqueous biological fluid. Osmotically effective osmagents useful for the present purpose include magnesium sulfate, magnesium chloride, sodium chloride, lithium chloride, potassium sulfate, sodium carbonate, sodium sulfite, lithium sulfate, potassium chloride, sodium sulfate, d-mannitol, urea, sorbitol, inositol, raffinose, sucrose, glycose, hydrophilic polymers such as cellulose polymers, mixtures thereof and the like. The osmagent is usually present in an excess amount, and it can be in any physical form, such as particle, powder, granule, and the like. The osmotic pressure in atmospheres of the osmagents suitable for the invention will be greater than zero and generally up to about 500 atm, or higher.

The optional hydrophilic polymer layer 16 is comprised of a swellable, hydrophilic polymer which interacts with water and aqueous biological fluids and swells to an equilibrium state. The polymers exhibit the ability to swell in water and retain a significant portion of the imbibed water within the polymer structure. The polymers swell or expand to a very high degree, usually exhibiting a 2 to 50 fold volume increase. The polymers can be noncross-linked or cross-linked. The swellable, hydrophilic polymers are in one presently preferred embodiment lightly cross-linked, such cross-links being formed by covalent ionic bonds or hydrogen bonds. The polymers can be of plant, animal or synthetic origin. Hydrophilic polymers suitable for the present purpose include poly(hydroxy alkyl methacrylate)having a molecular weight of from 30,000 to 5,000,000; poly(vinylpyrrolidone) having a molecular weight of form 10,000 to 360,000; anionic and cationic hydrogels; polyelectrolyte complexes; poly(vinyl alcohol) having a low acetate residual, cross-linked with glyoxal, formaldehyde, or glutaraldehyde and having a degree of polymerization from 200 to 30,000; a mixture of methylcellulose; cross-linked agar and carboxymethylcellulose; a water insoluble, water swellable copolymer produced by forming a dispersion of finely divided copolymer of maleic anhydride with styrene, ethylene, propylene, butylene or isobutylene cross-linked with from 0.001 to about 0.5 moles of saturated cross-linking agent per mole of maleic anhydride copolymer; water swellable polymers of N-vinyl lactams, and the like. Other polymers include polymers that from hydrogels such as Carbopol ® acidic carboxy polymers having a molecular weight of 450,000 to 4,000,000; Cyanamer ® polyacrylamides; cross-linked water swellable indene-maleic anhydride polymers, Goodrite ® polyacrylic acid polymers having a molecular weight of 80,000 to 200,000; Polyox ® polyethylene oxide polymers having molecular weight of 100,000 to 5,000,000 and higher; starch graft copolymers; Aqua-Keeps ® acrylate polymer polysaccharides composed of condensed glucose units such as diester cross-linked polyglucan, and the like. Representative polymers that from hydrogels are known to the prior art in U.S. Pat. Nos. 3,865,108 issued to Hartop; 4,002,173 issued to Manning; 4,207,893 issued to Michaels; and in *Handbook of Common Polymers*, by Scott and Roff, published by the Chemical Rubber Company, Cleveland, Ohio.

The device of the invention can be manufactured by standard techniques. For example, in one embodiment, the nicotine/alkaline salt formulation and optionally other ingredients are pressed into a solid possessing the approximate dimensions of the final device. The nicotine salt, the alkaline salt and other optional ingredients can be mixed into a solid or semisolid form by conventional methods such as ball milling, calendering, stirring or roll milling, pressed into the preselected shape and then coated with a thin semipermeable wall. In those embodiments utilizing the hydrophilic polymer layer 16, a layer of a hydrophilic polymer is placed in contact with the nicotine/alkaline salt formulation layer and the two layers surrounded with a semipermeable wall. The layering of the salt formulation and the hydrophilic polymer can be fabricated by conventional two-layer press techniques. The wall can be applied by molding, spraying or dipping the pressed shapes into a wall forming material. Another and presently preferred technique that can be used for applying the wall is the air suspension procedure. This procedure consists of suspending and tumbling the pressed agent and dry hydrophilic polymer in a current of air and a wall forming composition until the wall is applied to the pressed composite. The air suspension procedure is described in U.S. Pat. No. 2,799,241; *J. Am. Pharm. Assoc.*, Vol. 48, pp 451-59, (1979); and ibid, Vol. 49, pp 82-4, (1960). Other standard manufacturing procedures are described in *Modern Plastics Encyclopedia*, Vol. 46, pp 62-70, (1969); and in *Pharmaceutical Sciences*, by Remington, 14th Ed., pp 1626-78, (1970), published by Mack Publishing Company, Easton, Penna.

Exemplary solvents suitable for manufacturing the wall include inorganic and organic solvents that do not adversely harm the wall forming material, and the final device. The solvents broadly include members selected from the group consisting of aqueous solvents, alcohols, ketones, esters, ethers, aliphatic hydrocarbons, halogenated solvents, cycloaliphatic, aromatics, heterocyclic solvents, and mixtures thereof. Typical solvents include acetone, diacetone alcohol, methanol, ethanol, isopropyl acetate, n-butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethelene glycol monoethyl acetate, methylene dichloride, ethylene dichloride, propylene dichloride, carbon tetrachloride, nitroethane, nitropropane, tetrachloroethane, ethyl ether, isopropyl either, cyclohexane, cyclo-octane, benzene, toluene, naphtha, 1,4-dioxane, tetrahydrofuran, diglycol methyl ether, water and mixtures thereof such as acetone and water, acetone and methanol, acetone and ethyl alcohol, methylene dichloride and methanol, and ethylene dichloride and methanol, and mixtures thereof.

The expression, "passageway," as used herein, comprises means and methods suitable for releasing the agent from the system. The expression includes one or more aperture, orifice, bore or pores through wall 12 formed by mechanical procedures, or by eroding an erodible element, such as a gelatin plug, in the oral cavity. A detailed description of osmotic passageways and the maximum and minimum dimensions for a passageway are disclosed in U.S. Pat. Nos. 3,845,770 and 3,916,899, the disclosures of which are incorporated herein by reference. Preferably, 1 to 2 passageways 17 are provided in device 10 as shown in the Figures.

The expressions, "extended period of time," and "extended delivery period," as used herein, generally refers to periods greater than about 0.5 hours, preferably about 0.5 to 12 hours, more preferably about 0.5 to 6 hours, most preferably about 1-4 hours.

The following examples are merely illustrative of the present invention and should not be considered as limiting the scope of the invention in any way.

EXAMPLE 1

Osmotic therapeutic devices for the controlled continuous systemic delivery of nicotine base into the oral cavity for absorption through the oral mucosal membranes were made as follows: 0.73 g of nicotine bitartrate. 1.50 g of sodium bicarbonate, 83.27 g of polyethylene oxide (Polyox N-10), 5.00 g of hydroxypropylmethylcellulose (HPMC E-5), 3.00 g of sodium saccharin, 1.00 g of menthol, 1.00 g of peppermint oil, 3.00 g of spearmint oil, 1.00 g of anise oil and 0.5 g of magnesium stearate were mixed thoroughly and pressed on a Carver Press with a ½ inch oval punch using a pressure head of about 0.1 tons to produce a layer of the nicotine/alkaline salt formulation. The nicotine/alkaline salt formulation had a natural white color. The flavoring agents (i.e., saccharin, menthol, peppermint oil, spearmint oil and anise oil) were added to mask the objectionable taste of the nicotine base.

Next, the driving layer of the device was formulated by mixing 64.5 g of polyethylene oxide (Polyox Coag), 29.0 g NaCl, 5.0 g hydroxypropylmethylcellulose (HPMC E-5), 0.75 g of FDC Yellow Dye No. 5 and 0.25 g of FDC Blue Dye No. 1 as colorants and 0.5 g of magnesium stearate. The formulation was added to the Carver Press and pressed at about 0.5 tons to form a layer of hydrophilic polymer in contact with the nicotine/alkaline salt formulation layer. Bilayered 250 mg tablets were so produced, wherein the drug formulation layer weighted 150 mg and the hydrophilic polymer layer weighed 100 mg. Accordingly each tablet contained about 1.1 mg nicotine bitartrate. The hydrophilic polymer driving layer had a green color due to the yellow and blue dyes.

Next, the material for forming a semipermeable wall was made by blending 78.0 g of cellulose acetate having an acetyl content of 39.8% with 3550 ml of acetone, 320 ml of water and 31.2 g of polyethylene glycol (PEG 3350), 13.0 g of sorbitol, 2.6 g sodium saccharin, 1.3 g peppermint oil, 2.6 g spearmint oil, 0.65 g menthol and 0.5 g anise oil. The bilayered tablets were than pan coated with the cellulosic wall material in a 12 inch pan coater having a 1.2 kg charge until a 3.5 mil thick semipermeable wall surrounded each bilayered tablet. The coated tablets were dried for 24 hours at 32° C. Two 25 mil passageways were drilled through the semipermeable wall on the side of the coated tablets adjacent the nicotine/alkaline salt formulation layer. The PEG component of the wall material made the wall sufficiently translucent to clearly see the white drug formulation layer and the green hydrophilic polymer layer.

EXAMPLE 2

Osmotic therapeutic devices for the controlled continuous systemic delivery of nicotine base into the oral cavity for absorption through the oral mucosal membranes were made as follows: 2.30 g of nicotine bitartrate, 3.75 g of sodium bicarbonate, 41.20 g of polyethylene oxide (Polyox N-10), 2.50 g of hydroxypropylmethylcellulose (HPMC E-5), and 0.25 g of magnesium stearate were prepared by blending the ingredients into a homogenous blend, and then pressed into a solid mass. The salt layer had a weight of 150 mg and a white color.

Next, 100 mg of the same hydrophilic polymer composition used in Example 1 was added to the press (Carver Press set to a Stoke's hardness of 7 kp) and was compressed into a solid mass in contact with the nicotine salt-containing layer. The hydrophilic polymer layer had a green color providing a good color contrast with the white nicotine salt-containing layer.

The material for forming a semipermeable wall was made by blending 60.0 g of cellulose acetate having an acetyl content of 39.8% with 2740 ml of acetone. Then, 40.0 g hydroxypropylcellulose having a nominal molecular weight of 60,000 (Klucel EF) was dissolved in 240 ml of water. The acetone and water solutions were then blended to form a coating solution. The bilayered tablets were then pan coated with the cellulosic material using the same equipment and procedures described above in Example 1. Two 25 mil passageways were then drilled through the semipermeable wall on the side of the coated tablets adjacent the nicotine/alkaline salt formulation layer. The Klucel component of the wall material made the wall sufficiently translucent to clearly see the white drug formulation layer and the green hydrophilic polymer layer.

The devices were tested in three human subjects. Two of the subjects were each given a single device to retain in their mouths over the testing period. The other subject was given two devices to retain in his mouth over the testing period. Blood plasma concentrations were taken from all three subjects at two hours and four hours following initial placement in the mouth. After four hours, all three subjects removed the devices which were than tested for residual nicotine salt content. The first subject's device delivered 2.26 mg of nicotine based on its residual nicotine content. The third subject's device delivered 2.77 mg of nicotine based on its residual nicotine content. The second subject (which subject had two devices retained in his mouth at once) received 6.8 mg of nicotine based on the residual nicotine content in the two devices.

Immediately following removal of the devices at the end of four hours, the first two subjects were given new devices which were retained in their mouths for an additional four hours. Again, the first subject was given a single device while the second subject was given two devices. Blood plasma concentrations in the first two subjects were measured again at six and eight hours. The accompanying FIG. 5 depicts the blood plasma concentration of nicotine in the three subjects during the test period. FIG. 5 illustrates that the nicotine blood plasma levels can be elevated roughly two-fold by doubling the number of devices given to the patient. Those skilled in the art will appreciate that the nicotine blood plasma levels can also be increased by increasing the loading of the nicotine salt in layer 14.

EXAMPLE 3

Osmotic therapeutic devices for systemically delivering nicotine base through oral mucosal membranes in the oral cavity were manufactured as follows: first a 150 mg composition comprising 2.2% nicotine bitartrate, 1.5% $NaHCO_3$, 81.8% polyethylene oxide (Polyox N-10), 5.0% hydroxypropylmethylcellulose (HPMC E-5) 3.0% of Na saccharin, 1.0% menthol, 1.0% peppermint oil, 3.0% spearmint oil, 1.0% anise oil and 0.5% magnesium stearate was prepared by blending the ingredients into a homogenous blend, and then pressed into a solid mass in a Carver Press set to a Stoke's hardness of 7 kp. The resulting salt layer had a white color.

Next, 100 mg of the same hydrophilic polymer composition used in Example 1 was added to the press and was compressed into a solid mass in contact with the nicotine salt-containing layer. The hydrophilic polymer layer had a green color providing a good color contrast with the white nicotine salt-containing layer. Then, the bilayered tablets were coated with a semipermeable polymeric wall using the same coating composition and procedures described in Example 1. The PEG component of the wall material made the wall translucent, making it possible to see both the white drug layer and the green hydrophilic polymer layer within the inner compartment of the device. Two osmotic passageways, each having a diameter of 25 mils, were drilled through the wall facing the nicotine salt-containing layer for delivering nicotine base from the device.

EXAMPLE 4

Oral osmotic therapeutic devices for delivering nicotine base were made following the procedures of Example 1, except in this example, no flavoring agents were used. The drug formulation layer in each of the tablets weighted 150 mg and contained 0.73% nicotine bitartrate, 92.27% Polyox N-10, 5.00% HPMC E-5, 1.50% sodium bicarbonate and 0.50% magnesium stearate. The hydrophilic polymer layer in each of the tablets weighted 100 mg and had the same composition described in Example 1. The bilayered tablets were coated with a semipermeable wall 3.5 mils thick using the procedures described in Example 1. The wall was composed of 60% cellulose acetate having an acetyl content of 39.8% and 40% PEG 3350, formed form a solvent consisting essentially of 90% acetone and 10% water. Two passageways, each having a diameter of 25 mils, were drilled in the side of the devices adjacent the drug formulation layer.

EXAMPLE 5

Oral osmotic therapeutic devices for delivering nicotine base were made following the procedures of Example 4. The drug formulation layer in each of the tablets weighted 150 mg and contained 2.2% nicotine bitartrate, 90.8% Polyox N-10, 5.0% HPMC E-5, 1.5% sodium bicarbonate and 0.5% magnesium stearate. The hydrophilic polymer layer in each of the tablets weighed 100 mg and had the same composition described in Example 1. The bilayered tablets were coated with a semipermeable wall having a thickness of 3.5 mils using the procedures described in Example 1. The wall had the same composition described above in Example 4. Two passageways, each having a diameter of 25 mils, were drilled in the side of the devices adjacent the drug formulation layer.

EXAMPLE 6

Oral osmotic therapeutic devices for delivering nicotine base were made following the procedures described above in Examples 4 and 5, except in this example, the semipermeable wall is comprised of a two layer laminate structure including an underlying supporting layer and an outer semipermeable membrane layer. The drug formulation layer in each of the tablets weighted 150 mg and contained 20.47% nicotine bitartrate, 66.53% Polyox N-10, 5.00% HPMC E-5, 7.50% sodium bicarbonate and 0.50% magnesium stearate. The hydrophilic polymer layer in each of the tablets weighed 100 mg and contained 64.3% Polyox Coag, 29.2% NaCl, 5.0% HPMC E-5, 1.0% ferric oxide and 0.5% magnesium stearate. The hydrophilic polymer driving layer had a reddish-brown color due to the ferric oxide.

The bilayered tablets were then coated using a 12 inch pan coater having a 1.2 kg charge. The membrane support layer was composed of 60% Klucel EF and 40% cellulose acetate having an acetal content of 39.8%. Immediately following coating with the cellulose acetate-based supporting layer, the tablets were coated in a similar pan coater with a semipermeable membrane layer composed of 60% cellulose acetate having an acetal content of 39.8% and 40% Klucel EF. The Klucel component in the support layer and the semipermeable membrane layer made the wall translucent, making it possible to see both the white drug formulation layer and the reddish-brown hydrophilic polymer layer within the inner compartment of the device. Two osmotic passageways, each having a diameter of 25 mils, were drilled through the walls facing the nicotine salt-containing layer in each of the devices.

While there have been described and pointed out features of the invention as applied to the presently preferred embodiments, those skilled in the art will appreciate that various modifications, changes, additions and omissions in the systems illustrated and described can be made without departing from the spirit and scope of the invention as defined in the appended claims.

We claim:

1. An osmotic device for the controlled systemic delivery of nicotine base through an oral mucosal membrane in an oral cavity over an extended delivery period, including: a semipermeable wall surrounding and forming a compartment containing a nicotine salt which is capable of reacting with an aqueous fluid to form nicotine base, the wall being formed of a material which is permeable to the passage of an aqueous fluid present in the oral cavity, and a passageway through the semipermeable wall for delivering the nicotine base formed in the compartment to the oral mucosal membrane, wherein the device when in operation in the oral cavity imbibes the aqueous fluid through the wall into the compartment, thereby initiating a chemical reaction between the nicotine salt and the aqueous fluid to produce nicotine base which is delivered from the compartment through the passageway and into the oral cavity over time.

2. The osmotic device of claim 1, wherein the nicotine salt is selected from the group consisting of nicotine hydrochloride, nicotine dihydrochloride, nicotine sulfate, nicotine monotartrate, nicotine bitartrate, nicotine salicylate and nicotine zinc chloride monohydrate.

3. The osmotic device of claim 1, wherein the nicotine salt is selected from the group consisting of nicotine monotartrate and nicotine bitartrate.

4. The osmotic device of claim 1, wherein the compartment also contains an alkaline salt which is capable of reacting with the nicotine salt in the presence of the aqueous fluid to form nicotine base.

5. The osmotic device of claim 4, wherein the alkaline salt is osmotically active.

6. The osmotic device of claim 4, wherein the alkaline salt has a pH of greater than about 7.

7. The osmotic device of claim 4, wherein the alkaline salt is selected from the group consisting of sodium carbonate, sodium bicarbonate, potassium carbonate, potassium bicarbonate, trisodium phosphate, disodium hydrogen phosphate, sodium oxylate, sodium succinate, sodium citrate, and sodium salicylate.

8. The osmotic device of claim 4, wherein the alkaline salt comprises sodium bicarbonate.

9. The osmotic device of claim 1, wherein the device has a size and shape suitable for comfortably retaining the device in the oral cavity for the extended delivery period.

10. The osmotic device of claim 1, wherein the device has a smooth oval shape with an aspect ratio in the range of about 1.2:1 to about 3:1, a height of about 0.5 to about 10 mm, and a volume of less than about 2 cm$^3$.

11. The osmotic device of claim 1, wherein the compartment further contains a gelling agent which substantially prevents the wall from collapsing under conditions of use in the oral cavity.

12. The osmotic device of claim 11, wherein the gelling agent is selected from the group consisting of acacia, agar-agar, calcium carrageenan, alginic acid, algin, agarose powder, collagen, colloidal magnesium silicate, colloidal silicon dioxide, cross-linked polyacrylic acid, polyvinyl pyrrolidone, sodium carboxymethylcellulose, hydroxyethylcellulose, hydroxypropylcellulose, hydroxypropylmethylcellulose, polyethylene oxide, pectin, gelatin and calcium silicate.

13. The osmotic device of claim 11, wherein the gelling agent is selected from the group consisting of polyethylene oxide and hydroxypropylmethylcellulose.

14. The osmotic device of claim 1, wherein compartment contains a layer of a hydrophilic polymer.

15. The osmotic device of claim 14, wherein the hydrophilic polymer is a cross-linked hydrogel.

16. The osmotic device of claim 1, wherein the extended delivery period is about 0.5 to 12 hours.

17. The osmotic device of claim 1, wherein the extended delivery period is about 1 to 6 hours.

18. A method of systemically delivering nicotine base through an oral mucosal membrane in an oral cavity over an extended delivery period comprising:

placing into the oral cavity an osmotic device including a semipermeable wall surrounding and forming a compartment containing a nicotine salt which is capable of reacting with an aqueous fluid present in the oral cavity to form nicotine base, the wall being permeable to the aqueous fluid, the device having a passageway through the semipermeable wall;

delivering the nicotine base formed in the compartment to the oral mucosal membrane at a controlled rate over the extended delivery period by imbibing the aqueous fluid through the wall into the compartment, thereby initiating a chemical reaction between the nicotine salt and the aqueous fluid to produce nicotine base and delivering the nicotine base from the compartment through the passageway over the extended delivery period.

19. The method of claim 18, wherein the nicotine salt is selected from the group consisting of nicotine hydrochloride, nicotine dihydrochloride, nicotine sulfate, nicotine monotartrate, nicotine bitartrate, nicotine salicylate and nicotine zinc chloride monohydrate.

20. The method of claim 18, wherein the nicotine salt is selected from the group consisting of nicotine monotartrate and nicotine bitartrate.

21. The method of claim 18, wherein the compartment also contains an alkaline salt which is capable of reacting with the nicotine salt in the presence of the aqueous fluid to form nicotine base.

22. The method of claim 21, wherein the alkaline salt is osmotically active.

23. The method of claim 21, wherein the alkaline salt has a pH of greater than about 7.

24. The method of claim 21, wherein the alkaline salt is selected from the group consisting of sodium carbonate, sodium bicarbonate, potassium carbonate, potassium bicarbonate, trisodium phosphate, disodium hydrogen phosphate, sodium oxylate, sodium succinate, sodium citrate and sodium salicylate.

25. The method of claim 21, wherein the alkaline salt comprises sodium bicarbonate.

26. The method of claim 18, wherein the device has a smooth oval shape with an aspect ratio in the range of about 1.2:1 to about 3:1, a height of about 0.5 to about 10 mm, and a volume of less than about 2 cm$^3$.

27. The method of claim 18, wherein the extended delivery period is about 0.5 to 12 hours.

28. The method of claim 18, wherein the compartment further contains a gelling agent which substantially prevents the wall from collapsing under conditions of use in the oral cavity.

29. The method of claim 28, wherein the gelling agent is selected from the group consisting of acacia, agar-agar, calcium carrageenan, alginic acid, algin, agarose powder, collagen, colloidal magnesium silicate, colloidal silicon dioxide, cross-linked polyacrylic acid, polyvinyl pyrrolidone, sodium carboxymethylcellulose, hydroxyethylcellulose, hydroxypropylcellulose, hydroxypropylmethylcellulose, polyethylene oxide, pectin, gelatin and calcium silicate.

30. The method of claim 28, wherein the gelling agent is selected from the group consisting of polyethylene oxide and hydroxypropylmethylcellulose.

31. The method of claim 18, wherein the compartment contains a layer of a hydrophilic polymer.

32. The method of claim 31, wherein the hydrophilic polymer is a cross-linked hydrogel.

33. The method of claim 18, wherein the extended delivery period is about 0.5 to 12 hours.

34. The method of claim 18, wherein the extended delivery period is about 1 to 6 hours.

35. An osmotic device for the controlled systemic delivery of nicotine base through an oral mucosal membrane in an oral cavity over an extended delivery period including: a semipermeable wall surrounding and forming a compartment containing a nicotine salt which is capable or reacting with an aqueous fluid to form nicotine base, the wall being formed of a material which is permeable to the passage of an aqueous fluid present in the oral cavity, and a passageway through the semipermeable wall for delivering nicotine to the oral mucosal membrane, wherein the device when in operation in the oral cavity imbibes the aqueous fluid through the wall into the compartment, thereby converting the nicotine salt to nicotine base which is delivered through the oral mucosal membrane over time.

36. The osmotic device of claim 35, wherein the nicotine salt is selected from the group consisting of nicotine hydrochloride, nicotine dihydrochloride, nicotine sulfate, nicotine monotartrate, nicotine bitartrate, nicotine salicylate and nicotine zinc chloride monohydrate.

37. The osmotic device of claim 35, wherein the nicotine salt is selected from the group consisting of nicotine monotartrate and nicotine bitartrate.

38. The osmotic device of claim 35, wherein the compartment also contains an alkaline salt which is capable of enhancing the conversion of the nicotine salt to nicotine base.

39. The osmotic device of claim 38, wherein the alkaline salt is osmotically active.

40. The osmotic device of claim 38, wherein the alkaline salt has a pH of greater than about 7.

41. The osmotic device of claim 38, wherein the alkaline salt is selected fro mthe group consisting of sodium carbonate, sodium bicarbonate, potassium carbonate, potassium bicarbonate, trisodium phosphate, disodium hydrogen phosphate, sodium oxylate, sodium succinate, sodium citrate, and sodium salicylate.

42. The osmotic device of claim 38, wherein the alkaline salt comprises sodium bicarbonate.

43. The osmotic device of claim 35, wherein the device has a size and shape suitable for comfortably retaining the device in the oral cavity for the extended delivery period.

44. The osmotic device of claim 35, wherein the device has a smooth oval shape with an aspect ratio in the range of about 1.2:1 to about 3:1, a height of about 0.5 mm to about 10 mm, and a volume of less than about 2 cm$^3$.

45. The osmotic device of claim 35, wherein the compartment further contains a suspending or gelling agent which substantially prevents the wall from collapsing under conditions of use in the oral cavity.

46. The osmotic device of claim 45, wherein the suspending or gelling agent is selected from the group consisting of acacia, agar-agar, calcium carrageenan, alginic acid, algin, alginates, agarose powder, collagen, colloidal magnesium silicate, colloidal silicon dioxide, cross-linked polyacrylic acid, polyvinyl pyrrolidone, sodium carboxymethylcellulose, hydroxyethylcellulose, hydroxypropylcellulose, hydroxypropylmethylcellulose, polyethylene oxide, pectin, gelatin and calcium silicate.

47. The osmotic device of claim 45, wherein the suspending or gelling agent comprises hydroxypropylcellulose.

48. The osmotic device of claim 35, wherein the compartment contains a layer of a hydrophilic polymer.

49. The osmotic device of claim 48, wherein the hydrophilic polymer is a cross-linked hydrogel.

50. The osmotic device of claim 48, wherein the hydrophilic polymer is a polysaccharide.

51. The osmotic device of claim 35, wherein the extended delivery period is about 0.5 to 12 hours.

52. The osmotic device of claim 35, wherein the extended delivery period is about 1 to 6 hours.

53. The osmotic device of claim 35, wherein at least a portion of the nicotine salt is converted to nicotine base within the compartment and delivered through the passageway and into the oral cavity.

54. The osmotic device of claim 35, wherein at least a portion of the nicotine salt is converted to nicotine base outside the device and within the oral cavity.

55. A method of systemically delivering nicotine base through an oral mucosal membrane in an oral cavity over an extended delivery period comprising:
    placing into the oral cavity an osmotic device including a semipermeable wall surrounding and forming a compartment containing a nicotine salt which is capable of reacting with an aqueous fluid present in the oral cavity to form nicotine base, the wall being permeable to the aqueous fluid, the device having a passageway through the semipermeable wall;
    delivering the formed nicotine base to the oral mucosal membrane at a controlled rate over the extended delivery period by imbibing the aqueous fluid through the wall into the compartment, thereby converting the nicotine salt to nicotine base which is delivered through the oral mucosal membrane over the extended delivery period.

56. The method of claim 55, wherein the nicotine salt is selected from the group consisting of nicotine hydrochloride, nicotine dihydrochloride, nicotine sulfate, nicotine monotartrate, nicotine bitartrate, nicotine salicylate and nicotine zinc chloride monohydrate.

57. The method of claim 55, wherein the nicotine salt is selected from the group consisting of nicotine monotartrate and nicotine bitartrate.

58. The method of claim 55, wherein the nicotine salt is selected from the group consisting of nicotine monotartrate and nicotine bitartrate.

59. The method of claim 58, wherein the alkaline salt is osmotically active.

60. The method of claim 58, wherein the alkaline salt has a pH of greater than about 7.

61. The method of claim 58, wherein the alkaline salt is selected from the group consisting of sodium carbonate, sodium bicarbonate, potassium carbonate, potassium bicarbonate, trisodium phosphate, disodium hydrogen phosphate, sodium oxylate, sodium succinate, sodium citrate and sodium salicylate.

62. The method of claim 58, wherein the alkaline salt comprises sodium bicarbonate.

63. The method of claim 55, wherein the device has a smooth oval shape with an aspect ratio in the range of about 1.2:1 to about 3:1, a height of about 0.5 mm to about 10 mm, and a volume of less than about 2 cm$^3$.

64. The method of claim 55, wherein the extended delivery period is about 0.5 to 12 hours.

65. The method of claim 55, wherein the compartment further contains a suspending or a gelling agent which substantially prevents the wall from collapsing under conditions of use in the oral cavity.

66. The method of claim 65, wherein the suspending or gelling agent is selected from the group consisting of acacia, agar-agar, calcium carrageenan, alginic acid, algin, alginates, agarose powder, collagen, colloidal magnesium silicate, colloidal silicon dioxide, cross-linked polyacrylic acid, polyvinyl pyrrolidone, sodium carboxymethylcellulose, hydroxyethylcellulose, hydroxypropylcellulose, polyethylene oxide, pectin, gelatin and calcium silicate.

67. The method of claim 65, wherein the suspending or gelling agent comprises hydroxypropylcellulose.

68. The method of claim 55, wherein the compartment contains a layer of a hydrophilic polymer.

69. The method of claim 68, wherein the hydrophilic polymer is a cross-linked hydrogel.

70. The method of claim 68, wherein the hydrophilic polymer is a polysaccharide.

71. The method of claim 55, wherein the extended delivery period is about 0.5 to 12 hours.

72. The method of claim 55, wherein the extended delivery period is about 1 to 6 hours.

73. The method of claim 55, wherein at least a portion of the nicotine salt is converted to nicotine base within the compartment and delivered through the passageway and into the oral cavity.

74. The method of claim 55, wherein at least a portion of the nicotine salt is converted to nicotine base outside the device and within the oral cavity.

* * * * *